United States Patent [19]

Rainey et al.

[11] 4,400,542
[45] Aug. 23, 1983

[54] SYNTHESIS OF SUBSTITUTED PHENOLS

[75] Inventors: David K. Rainey; Michael M. Fanthorpe, both of Loughborough, England

[73] Assignee: Fisons Limited, London, England

[21] Appl. No.: 256,295

[22] Filed: Apr. 22, 1981

Related U.S. Application Data

[63] Continuation of Ser. No. 97,337, Nov. 26, 1979, abandoned.

[30] Foreign Application Priority Data

Dec. 5, 1978 [GB] United Kingdom ............... 47180/78

[51] Int. Cl.$^3$ ..................... C07C 45/68; C07C 41/835
[52] U.S. Cl. ..................................... 568/315; 568/337
[58] Field of Search ......................... 568/315, 316, 337

[56] References Cited

U.S. PATENT DOCUMENTS 3,467,715  9/1969  Broadbent et al. .................. 568/315
3,846,498  11/1974 Wild et al. .......................... 568/315
4,101,585  7/1978  Burckhardt et al. ................ 568/315

OTHER PUBLICATIONS

Goichiro et al., Chem. Abst., vol. 47, #8316a.
Morris et al., Organic Chem., pp. 346–347, (1966).
Worden et al., J. Heterocycl. Chem., 1969, 6(2), pp. 191–198, (1969).
Shridhor, Chem. Abst., vol. 38, #4258$^5$ (1944).

Primary Examiner—James H. Reamer
Attorney, Agent, or Firm—Merriam, Marshall & Bicknell

[57] ABSTRACT

There is described a process for the production of a 4,6-diacetyl resorcinol having an alkyl C 1 to 6 or an alkenyl C 2 to 6 group in the 2-position, which comprises reacting 4,6-diacetyl resorcinol with an alkyl C 1 to 6- or an alkenyl C 2 to 6- halide.

The product 4,6-diacetyl resorcinols are useful as intermediates in the production of pharmaceuticals. Certain of the product 4,6-diacetyl resorcinols are novel.

6 Claims, No Drawings

SYNTHESIS OF SUBSTITUTED PHENOLS

This is a continuation of application Ser. No. 97,337, filed Nov. 26, 1979, now abandoned.

This invention relates to a novel process for the production of certain 2-substituted 4,6-diacetyl resorcinols.

A number of 2-substituted 4,6-diacetyl resorcinols are known compounds, but in the past have been made by acetylation of the correspondingly substituted resorcinol. The production of the substituted resorcinols is a relatively complex process involving several process steps.

Thus 2-n-propyl-4,6-diacetyl resorcinol has in the past been produced from resorcinol by the following set of reactions:

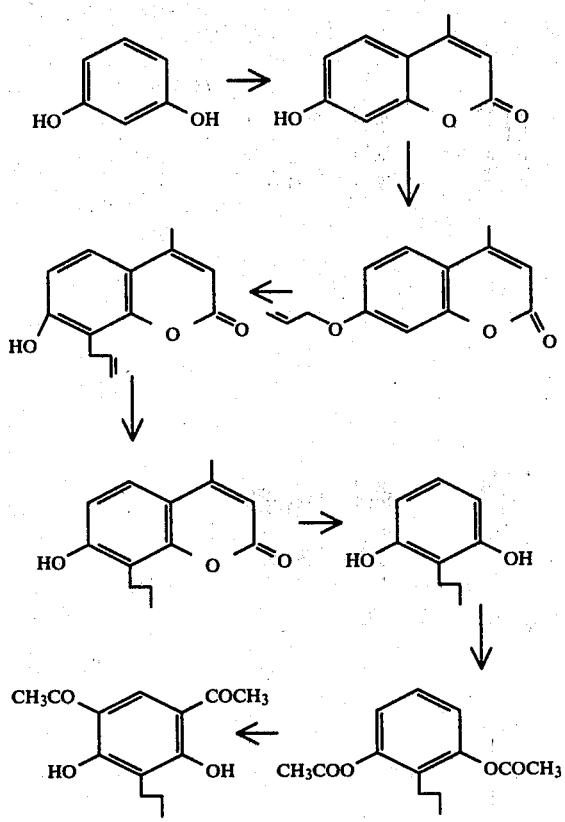

This seven step porcess can now be replaced by a two step process in which resorcinol is acetylated to produce 4,6-diacetyl resorcinol which can then be alkylated or alkenylated directly to produce the desired 2-alkyl- or 2-alkenyl-4,6-diacetyl resorcinol. Previous attempts to alkylate phenols have usually resulted in the production of a larger proportion of -O alkyl products than ring alkylated compounds. Furthermore the previous attempts to ring alkylate phenols have not included the alkylation of acetyl phenols; the presence of an acetyl group would be expected to produce a deactivating effect on the carbon atoms of the benzene ring.

Surprisingly we have now found that 2-substituted 4,6-diacetyl resorcinols can be obtained by the direct substitution of the easily obtained 4,6-diacetyl resorcinols.

According to the invention we provide a process for the production of a 4,6-diacetyl resorcinol having an alkyl C 1 to 6 or an alkenyl C 2 to 6 group in the 2-position, which comprises reacting a 4,6-diacetyl resorcinol with an alkyl C 1 to 6- or an alkenyl C 2 to 6- halide.

More specifically we provide a process for the production of a compound of formula I,

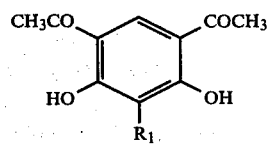

in which $R_1$ is alkyl C 1 to 6 or alkenyl C 2 to 6, which comprises reacting 4,6-diacetyl resorcinol with an alkyl C 1 to 6- or an alkenyl C 2 to 6- halide.

We particularly prefer $R_1$ to be alkyl C 2 to 4 or alkenyl C 3 to 4, e.g. propyl or allyl. We prefer $R_1$ to be a straight chain alkyl group.

The starting materials for the process, e.g. 4,6-diacetyl resorcinol, may be made by Friedel Crafts acetylation of resorcinol.

The alkyl or alkenyl halide may be a chloride, but is preferably an iodide or a bromide. In particular we prefer to use an alkyl halide. The reaction is preferably carried out at a temperature of from about 20 to 120° C., more preferably at from 50° to 120° C. and most preferably at the reflux temperature of the system. It is generally desirable to carry out the reaction at atmospheric pressure, but where it is desired to carry out the reaction at a temperature in excess of the boiling point of one of the components of the reaction system, pressures greater than atmospheric pressure may be used. The reaction is preferably carried out in a polar hydrogen bonding solvent; e.g. a lower alkanol/water mixture, water with a co-solvent (e.g. dichloroethane), but preferably in water alone. The reaction is also preferably carried out in the presence of a base, e.g. an alkali metal carbonate or bicarbonate or preferably an alkali metal hydroxide. Suitable bases include potassium hydroxide, sodium carbonate or sodium bicarbonate or preferably sodium hydroxide. The reaction may, if desired, be carried out in the presence of a catalyst, e.g. a catalytic amount of an inorganic iodide.

We prefer to use an excess of the alkyl- or alkenyl-halide with respect to the 4,6-diacetyl resorcinol starting material, e.g. a molar ratio of from about 1 to 1.5:1. We also prefer to use the base in a molar ratio of from about 1.8 to 2.2:1 with respect to the 4,6-diacetyl resorcinol starting material.

We prefer to use a 0.05 to 0.0125, and preferably about 0.025, initial molar concentration of the 4,6-diacetyl resorcinol in the reaction mixture when the reaction is carried out on a batch basis. The reaction may of course be modified to be carried out on a continuous basis, e.g. using a low concentration of 4,6-diacetyl resorcinol starting material in the solvent and using a temperature of from room temperature to below the reflux temperature of the solvent.

The alkyl and alkenyl 4,6-diacetyl resorcinols produced by the process of the invention are useful as intermediates, in processes known per se, e.g. by reaction with diethyl oxalate, for the production of certain benzodipyran- dicarboxylic acids which are of known utility as pharmaceuticals.

The compounds 2-allyl-4,6-diacetyl resorcinol and 2-iso-propyl-4,6-diacetyl resorcinol are new compounds and the invention also provides these compounds per se.

These new compounds are advantageous in that they are useful as intermediates in the production of particularly useful pharmaceuticals.

The invention is illustrated, but in no way limited by the following Examples.

EXAMPLE 1

2-Allyl-4,6-diacetylresorcinol 4,6-Diacetylresorcinol (19.4 g; 0.1 mole), sodium hydroxide (8.0 g; 0.2 mole) and allyl bromide (12.1 g; 9 ml; 0.1 mole) in water (160 ml) and 1,2-dichloroethane (150 ml) were stirred at reflux for 3 hours. The mixture was cooled to room temperature, the organic layer was separated and the aqueous layer was extracted with 1,2-dichloroethane (3×50 ml). The combined organic layers were dried (anhydrous sodium sulphate) and evaporated to give 2-allyl-4,6-diacetylresorcinol as a pink oil (9 g; 38%) which rapidly crystallised, m.p. 84°–86° C.

EXAMPLE 2

4,6-Diacetyl-2-n-propylresorcinol 4,6-Diacetylresorcinol (600 g; 3.09 mole), sodium hydroxide (247 g; 6.18 mole) and n-propyl bromide (645 g; 477 ml; 5.25 mole) in water (2.47 L) were stirred at reflux for 22 hours. The mixture was cooled to room temperature, diluted with water (2 L), and acidified with concentrated hydrochloric acid. Filtration gave a light brown solid which was washed with water (2 L), sucked dry and recrystallised from ethanol (3 times) to give a white crystalline solid (408 g), m.p. 84°–92° C. A portion (300 g) of the solid was recrystallised from chloroform (600 ml)/petroleum-ether (60°–80°; 1200 ml) to give 4,6-diacetyl-2-n-propylresorcinol (225 g; 30%) as a white crystalline solid, m.p. 97°–99° C.

EXAMPLE 3

2-Isopropyl 4,6-diacetyl resorcinol 4,6-Diacetyl resorcinol (9.7 g $5\times10^{-2}$ m), sodium hydroxide (4.0 g $1\times10^{-1}$ m) and i-propyl bromide (9.22 g $7.5\times10^{-2}$ m) in water (40 ml) were heated at reflux for 16 hours. A further aliquot (9.22 g) of i-propyl bromide was added and reflux continued for a further 30 hours. An oil separated which crystallised on standing, and was removed by filtration. Acidification of the mother liquors yielded no further product.

The solid was recrystallised from isopropanol to give the title compound as white flakes (3.0 g). Addition of water to the mother liquors at reflux, and cooling gave a further crop of the title compound (2.0 g). The two crops were combined (5.0 g 42%) m.p. 132°–133°.

EXAMPLE 4

2-n-Butyl-4,6-diacetyl resorcinol 4,6-Diacetyl resorcinol (485 g, 2.5 m) sodium hydroxide (220 g, 5 m), 1-iodobutane (285 ml, 2.5 m) and water (2 l) were heated on a steam bath for 16 hours, cooled to 20° and the yellow-white precipitate filtered and washed with water. The solid was washed with dilute hydrochloric acid, extracted into chloroform (2×1.5 l) and the chloroform solution washed with water (2 l) and brine (1 l), then dried (anhyd. Na$_2$SO$_4$). Filtration and removal of solvent gave an oil (420 g) which crystallised on standing.

EXAMPLE 5

4,6-diacetyl-2-allylresorcinol

A 5.75% solution of allyl bromide in dichloroethane (500 ml) was added slowly (over 3 hours 20 minutes to a hot (65° C.) solution of 4,6-diacetyl resorcinol (12 g) in aqueous sodium hydroxide solution (4.94 g sodium hydroxide in 72 mls of water). The lower organic layer consisting of the product, 4,6-diacetyl-2-allylresorcinol, dissolved in dichloroethane was continually removed.

Evaporation of the combined organic layer gave the product (8.91 g) in 69.7% yield.

What we claim is:

1. A process for the production of a compound of formula I,

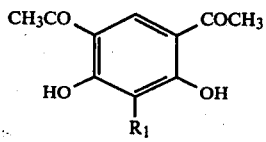

in which R$_1$ is alkyl C 1 to 6,
which comprises reacting 4,6-diacetyl resorcinol with an alkyl C 1 to 6- bromide or iodide in a polar hydrogen bonding solvent at a temperature of from 20° to 120° C.

2. A process according to claim 1, when carried out in the presence of a base.

3. A process according to claim 2, wherein the solvent is water.

4. A process according to claim 2, wherein the molar ratio of alkyl-halide to the 4,6-diacetyl resorcinol starting material is from 1 to 1.5:1.

5. A process according to claim 2, wherein base is used in a molar ratio of from 1.8 to 2.2:1 with respect to the 4,6-diacetyl resorcinol starting material.

6. 2-Allyl-4,6-diacetyl resorcinol or 2-iso-propyl-4,6-diacetyl resorcinol.

* * * * *